United States Patent
O'Caoimh et al.

(10) Patent No.: US 8,349,278 B2
(45) Date of Patent: Jan. 8, 2013

(54) APPARATUS FOR WITHDRAWING A LIQUID SAMPLE FROM SELECTED ONES OF A PLURALITY OF CONTAINERS

(75) Inventors: Ronan Patrick O'Caoimh, Delgany (IE); James Walsh, Monkstown (IE); Brendan Kevin Farrell, Glenealy (IE); Rory Peter Nealon, Blackrock (IE); Josef Georg Hubert Wiehe, Hoexter (DE)

(73) Assignee: TCOAG Ireland Limited, Dublin (IE)

( * ) Notice: Subject to any disclaimer, the term of this patent is extended or adjusted under 35 U.S.C. 154(b) by 355 days.

(21) Appl. No.: 12/515,043

(22) PCT Filed: Nov. 15, 2007

(86) PCT No.: PCT/IE2007/000111
§ 371 (c)(1),
(2), (4) Date: Mar. 23, 2010

(87) PCT Pub. No.: WO2008/059470
PCT Pub. Date: May 22, 2008

(65) Prior Publication Data
US 2010/0212437 A1    Aug. 26, 2010

(30) Foreign Application Priority Data
Nov. 15, 2006  (IE) .................................. S2006/0824

(51) Int. Cl.
*G01N 35/10* (2006.01)
*G01N 1/14* (2006.01)
*C12M 1/26* (2006.01)

(52) U.S. Cl. .............. 422/512; 422/63; 422/65; 436/43; 436/47; 436/49; 436/54; 73/864.43; 73/864.24; 141/329

(58) Field of Classification Search ........................ None
See application file for complete search history.

(56) References Cited

U.S. PATENT DOCUMENTS

| | | | |
|---|---|---|---|
| 5,935,523 A * | 8/1999 | McCandless et al. | ........ 422/510 |
| 2003/0226391 A1 | 12/2003 | Sanderson | |
| 2006/0216208 A1 * | 9/2006 | Li et al. | ......... 422/100 |

FOREIGN PATENT DOCUMENTS

| | | |
|---|---|---|
| DE | 10048643 A1 | 5/2001 |
| WO | 9118551 A1 | 12/1991 |
| WO | 9711347 A1 | 3/1997 |
| WO | 02103324 A2 | 12/2002 |
| WO | 2007051919 A1 | 5/2007 |

* cited by examiner

*Primary Examiner* — Kathryn Wright
(74) *Attorney, Agent, or Firm* — Sughrue Mion, PLLC

(57) ABSTRACT

Apparatus (1) for withdrawing respective liquid samples from vials (2) which are closed by closure caps (4) includes a plurality of racks (7) for accommodating the vials (2). A device (10) including a housing (25) is slideably carried on a gantry (9) which in turn is slideably carried on guide tracks (12) to provide two degrees of movement of the device (10) for selective alignment of the device (10) with the vials (2). An abutment member (43) is driven vertically by a second gearwheel (51) by a drive shaft (27) through a first gearwheel (40) and a dog clutch (52). A cannula which is secured within a first gear rack (33) is driven vertically by the first gearwheel (40). On engagement of the abutment member (43) with the closure cap (4) of the selected vial (2), the clutch (52) decouples the second gearwheel (51) from the first gearwheel (40) so that the cannula (28) is urgeable through the closure cap (4) into the vial (2).

22 Claims, 12 Drawing Sheets

Figure 1:
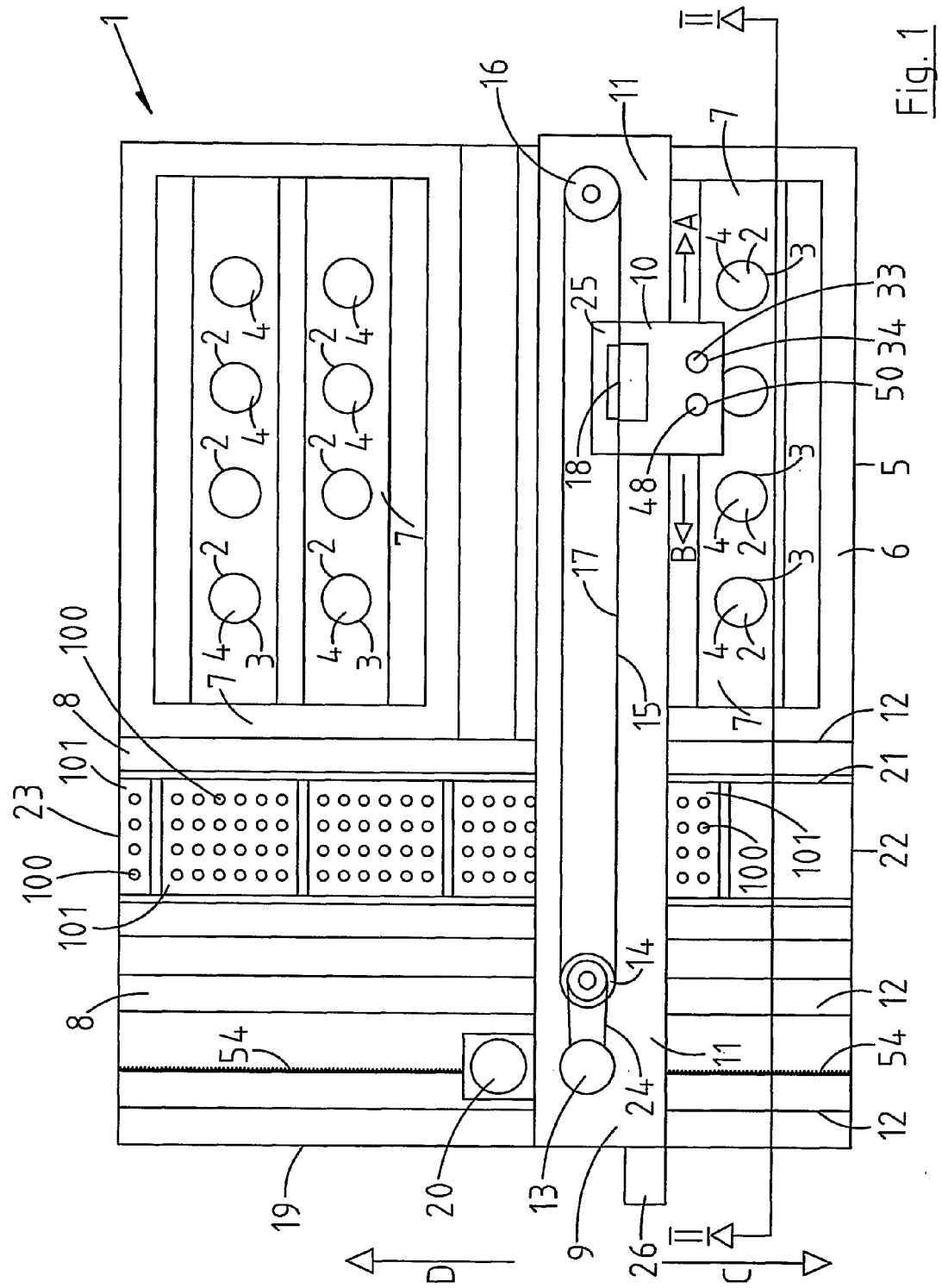

APPARATUS FOR WITHDRAWING A LIQUID SAMPLE FROM SELECTED ONES OF A PLURALITY OF CONTAINERS

The present invention relates to a device for withdrawing a liquid sample from a container or for discharging a liquid sample into a container, and the invention also relates to apparatus for withdrawing liquid samples from respective ones of a plurality of containers or for discharging liquid samples into respective ones of a plurality of containers.

Samples of bodily fluids, for example, blood, blood plasma, urine and other such bodily fluids are commonly stored in a vial when withdrawn from a subject. In order to analyse such bodily fluids, a sample of the bodily fluid is required to be placed in suitable chemical analytical apparatus, and in general, such chemical analytical apparatus require that the liquid sample be placed in a specific type of vessel, cuvette or well suitable for use in the particular chemical analytical apparatus. Commonly, such chemical analytical apparatus require that the liquid sample be placed in a cuvette or a well in a well plate. This requires withdrawing a sample of the bodily fluid from the vial and transferring it into a cuvette or well. Typically, the transfer of the bodily fluid is carried out by pipetting a suitable size sample of the bodily fluid into a cannula type pipette, and the liquid sample is then discharged from the pipette into the cuvette or well or other such vessel. This can be quite a slow and time consuming task.

Mechanisation of the task of transferring liquid samples from such vials to such cuvettes, wells or of such vessels has been hindered due to the fact that vials which are used by doctors and nurses for collecting the liquid samples from subjects tend to vary quite considerably in size, and in particular in height. Therefore, it is necessary to manually arrange the vials of liquid samples so, that vials of substantially similar height are located side by side, however, even with such manual arrangement of the vials, due to the extensive range of shapes and sizes of such vials, it is virtually impossible to have two vials of identical dimensions in the one batch of vials. This, thus, makes it particularly difficult to mechanise the withdrawal and transfer of samples from vials to corresponding cuvettes or wells.

A further complication in the mechanisation of the transfer of such samples from vials to corresponding cuvettes or wells results from the fact that in general all such vials are sealably closed by a closure element, which typically, is provided by a bung of rubber or of a rubber type material which is sealably engaged in an open mouth of the vial for sealably closing the vial. The rubber type material of the bung is adapted to be penetrable by a pointed cannula of the pipette. However, the rubber type material of such bungs is such as to be effectively self-sealing so that when the cannula of the pipette is subsequently withdrawn from the bung, the residual bore through the bung formed by the cannula effectively seals itself. This, however, adds further to the problems of mechanising the transfer of liquid samples from vials to cuvettes, wells or other such vessels, since the bung engages the cannula of the pipette with a relatively tight friction grip. While this, in general, does not cause any serious difficulties when inserting the cannula of the pipette into the vial through the bung, unfortunately, withdrawal of the cannula is virtually impossible without displacing the bung from the vial or displacing the vial from a rack or other support in which the vial is supported. Thus, in order to facilitate withdrawal of the cannula of a pipette from the bung of a vial, it is necessary to provide a device for holding down the bung of the vial while the cannula is being withdrawn therefrom. However, as mentioned above, due to the large variety of shapes and sizes of vials, and in particular the large variety of heights of such vials, it is impossible to provide a holding down device which will operate over a range of heights of vials. This also prevents the efficient mechanisation of the transfer of liquid samples from vials to cuvettes, wells or other such vessels of a chemical analytical apparatus, unless the vials are manually arranged so that adjacent vials are of substantially similar height. This is a time consuming task, and in many cases is largely impossible due to the large variety of shapes, sizes and heights of vials in which bodily fluids are collected.

There is therefore a need for a device for withdrawing a liquid sample from a container which addresses some of these problems, and there is also a need for apparatus for withdrawing liquid samples from a plurality of respective containers which similarly addresses some of these problems.

The present invention is directed towards providing a device for withdrawing a liquid sample from a container or for discharging a liquid sample into another container, and the invention is also directed towards apparatus for withdrawing liquid samples from respective ones of a plurality of containers or for discharging a liquid sample into respective ones of a plurality of containers.

According to the invention there is provided a device for withdrawing a liquid sample from a container or for discharging a liquid sample into a container, the device comprising a cannula for extending into the container, an abutment means for engaging one of the container and a closure element closing an open mouth thereof, and a drive transmission means through which the cannula and the abutment means are driven, the drive transmission means being operable for simultaneously urging the cannula and the abutment means towards the container, and being responsive to the abutment means engaging one of the container and the closure element for urging the cannula relative to the abutment means into the container with the abutment means in engagement with the one of the container and the closure element.

Preferably, the drive transmission means is operable for simultaneously urging the cannula and the abutment means away from the container in response to the cannula being withdrawn from the container.

Advantageously, a retaining means is provided for retaining the abutment means in engagement with the one of the container and the closure element thereof during movement of the cannula relative to the abutment means in a direction outwardly of the container.

In one embodiment of the invention the retaining means retains the abutment means in engagement with the one of the container and the closure element thereof during movement of the cannula relative to the abutment means in a direction into the container.

In another embodiment the drive transmission means comprises a first transmission means for driving the cannula, and a second transmission means for driving the abutment means, the second transmission means being driven by the first transmission means through a clutch means.

Preferably, the clutch means is responsive to the abutment means engaging the one of the container and the closure element thereof for decoupling the second transmission means from the first transmission means:

Advantageously, the second transmission means is co-operable with the retaining means when the second transmission means is decoupled from the first transmission means for retaining the abutment means in engagement with the one of the container and the closure element thereof.

Ideally, the clutch means is responsive to the distance through which the cannula is moved relative to the abutment means in a direction outwardly of the container being substantially similar to the distance through which the cannula has been previously moved relative to the abutment means in a direction inwardly into the container after engagement of the abutment means with the one of the container and the closure element thereof for recoupling the second transmission means to the first transmission means.

In one embodiment of the invention the clutch means comprises a dog clutch.

In another embodiment of the invention the first transmission means comprises a first drive transmission element, and the second drive transmission means comprises a second drive transmission element, the clutch comprising the first and second drive transmission elements and an engagement means extending from one of the first and second drive transmission elements for releasably engaging a corresponding receiving means on the other one of the first and second drive transmission elements for selectively transmitting drive from the first drive transmission element to the second drive transmission element.

Advantageously, a bearing means is provided on the one of the first and second drive transmission elements in which the receiving means is located for accommodating relative movement between the engagement means and the bearing means, for in turn accommodating relative movement between the first and second drive transmission elements. Preferably, the bearing means comprises a bearing surface extending from the receiving means. Ideally, the bearing surface is of length extending from the receiving means a distance sufficient to accommodate the maximum distance of relative movement of the cannula relative to the abutment means in a direction inwardly into the container.

In one embodiment of the invention an urging means is provided for urging the engagement means into engagement with the receiving means. Preferably, the urging means comprises a spring urging means for urging the second drive transmission element into engagement with the first drive transmission element. Advantageously, the engagement means and the receiving means are located on respective adjacent radial faces of the first and second drive transmission elements.

In one embodiment of the invention the first drive transmission element comprises a first gearwheel engageable with a first gear rack associated with the cannula. Preferably, the cannula is secured to the first gear rack.

Advantageously, the ratio of the linear distance traveled by the first gear rack for each unit angular displacement of the first gearwheel is such that the angular displacement of the first gearwheel required to drive the first gear rack a distance corresponding to the maximum distance of relative movement between the cannula and the abutment means in a direction inwardly into the container is less than 360°.

In another embodiment of the invention the second drive transmission element comprises a second gearwheel engageable with a second gear rack associated with the abutment means. Preferably, the abutment means is secured to the second gear rack.

In another embodiment of the invention the retaining means comprises a third gear rack with which the second gearwheel is engageable, the third gear rack being fixed relative to the second gearwheel for preventing rotation thereof when the second gearwheel is in engagement therewith. Preferably, the second gearwheel is simultaneously engageable with the second gear rack and the third gear rack in response to the abutment means engaging the one of the container and the closure element thereof.

In another embodiment of the invention the drive transmission means comprises a drive shaft, and the first transmission means is mounted on the drive shaft for receiving drive therefrom. Preferably, the first transmission means is keyed to the drive shaft. Advantageously, the second transmission means is rotatably mounted on the drive shaft.

In one embodiment of the invention the cannula is adapted for penetrating the closure element to extend into the container through the closure element. Preferably, the drive transmission means is responsive to the abutment means abutting the closure element of the container for urging the cannula relative to the abutment means through the closure element into and out of the container with the abutment means in engagement with the closure element for preventing displacement of the closure element.

In another embodiment of the invention the cannula is adapted for withdrawing a liquid sample from the container. Preferably, the cannula is adapted for withdrawing a liquid sample from a vial.

The invention also provides apparatus for facilitating withdrawing liquid samples from respective ones of a plurality of containers or for discharging a plurality of liquid samples into respective ones of a plurality of containers, the apparatus comprising a rack for holding the containers, and the device according to the invention for withdrawing a liquid sample from a container or for discharging a liquid sample into a container, the device being mounted on the apparatus above the rack, and being moveable relative to the rack for selective alignment with the respective ones of the containers and being mounted so that the cannula and the abutment means are simultaneously urgeable towards a selected one of the containers, the drive transmission means of the device being responsive to the abutment means engaging the one of the selected container and the closure element thereof for urging the cannula relative to the abutment means into the selected container with the abutment means in engagement with the one of the selected container and the closure element thereof.

In one embodiment of the invention the rack is an elongated rack, and a first guide means is provided for guiding the device along the rack for sequential selective alignment of the device with the respective containers in the rack. Advantageously, a first drive means is provided for driving the device along the first guide means.

In another embodiment of the invention a plurality of spaced apart parallel elongated racks are located in the apparatus, and a second guide means is provided for guiding the device transversely across the racks for selective alignment therewith. Preferably, a second drive means is provided for driving the device along the second guide means.

In another embodiment of the invention a third drive means is provided for providing drive to the cannula and the abutment means through the drive transmission means.

In another embodiment of the invention the apparatus comprises a base and the racks for the containers are mounted on the base.

In another embodiment of the invention a gantry is supported over the racks, the first guide means extending longitudinally along the gantry and the device is mounted on the gantry and is urgeable along the gantry on the first guide means. Preferably, the gantry is urgeable along the second guide means for selective alignment of the device with the respective racks.

In one embodiment of the invention the drive transmission means is operable for simultaneously urging the cannula and the abutment means away from the selected container in response to the cannula being withdrawn from the container.

In another embodiment of the invention a retaining means is provided for retaining the abutment means in engagement with the selected one of the containers and the closure element thereof during movement of the cannula relative to the abutment means in a direction outwardly of the container.

Preferably, the retaining means retains the abutment means in engagement with the selected one of the containers and the closure element thereof during movement of the cannula relative to the abutment means in a direction into the container.

The advantages of the invention are many. A particularly important advantage of the invention is that the device according to the invention and also the apparatus according to the invention is suitable for use in withdrawing liquid samples from vials or other such containers of different heights, even where the vials or containers of different heights are located adjacent each other. This is achieved by virtue of the fact that the cannula and the abutment means are simultaneously urged towards the container, and move in unison with each other until the abutment means engages either the container or a closure element of the container. Due to the fact that the drive transmission means is responsive to the abutment means engaging either the container or the closure element for urging the cannula relative to the abutment means into the container or through the closure element into the container, the height of the vial or other such container at which the abutment means engages the container or the closure element is irrelevant, since both the abutment means and the cannula move in unison until the abutment means engages the container or the closure element, as the case may be.

Furthermore, since the abutment means remains in engagement with the closure element or the container until the cannula has been withdrawn from the closure element, the cannula is readily easily disengaged from the vial and the closure element after the liquid sample has been pipetted from or into the vial or container, as the case may be without displacing the closure element relative to the vial or container, and without displacing the vial or container relative to its support. Both of these advantages are achieved by virtue of the fact that the cannula and the abutment means move in unison until the abutment means engages the container or the closure element thereof and only then does the cannula move relative to the abutment means into the container. Furthermore, by virtue of the fact that the abutment means is retained in engagement with the abutment means until the cannula has been withdrawn from the closure element, and the cannula and abutment means again move in unison away from the container, liquid samples can be readily easily pipetted into and from the containers irrespective of the height of the containers, and irrespective of the height of adjacent containers supported in the apparatus.

The provision of the retaining means ensures that the abutment means remains in engagement with the closure element or the container, as the case may be, until the cannula has been completely withdrawn from the closure element. By providing the drive means in the form of respective first and second drive elements whereby the first drive element drives the cannula and the second drive element drives the abutment means and in particular, by driving the second drive element through the first drive element, permits the inclusion of a clutch means between the first and second drive elements, which in turn permits the first drive element to drive the cannula relative to the abutment means. By providing the clutch means as a dog clutch has a particularly important advantage in that it provides for relatively simple construction of the device and apparatus according to the invention.

Figure 2:
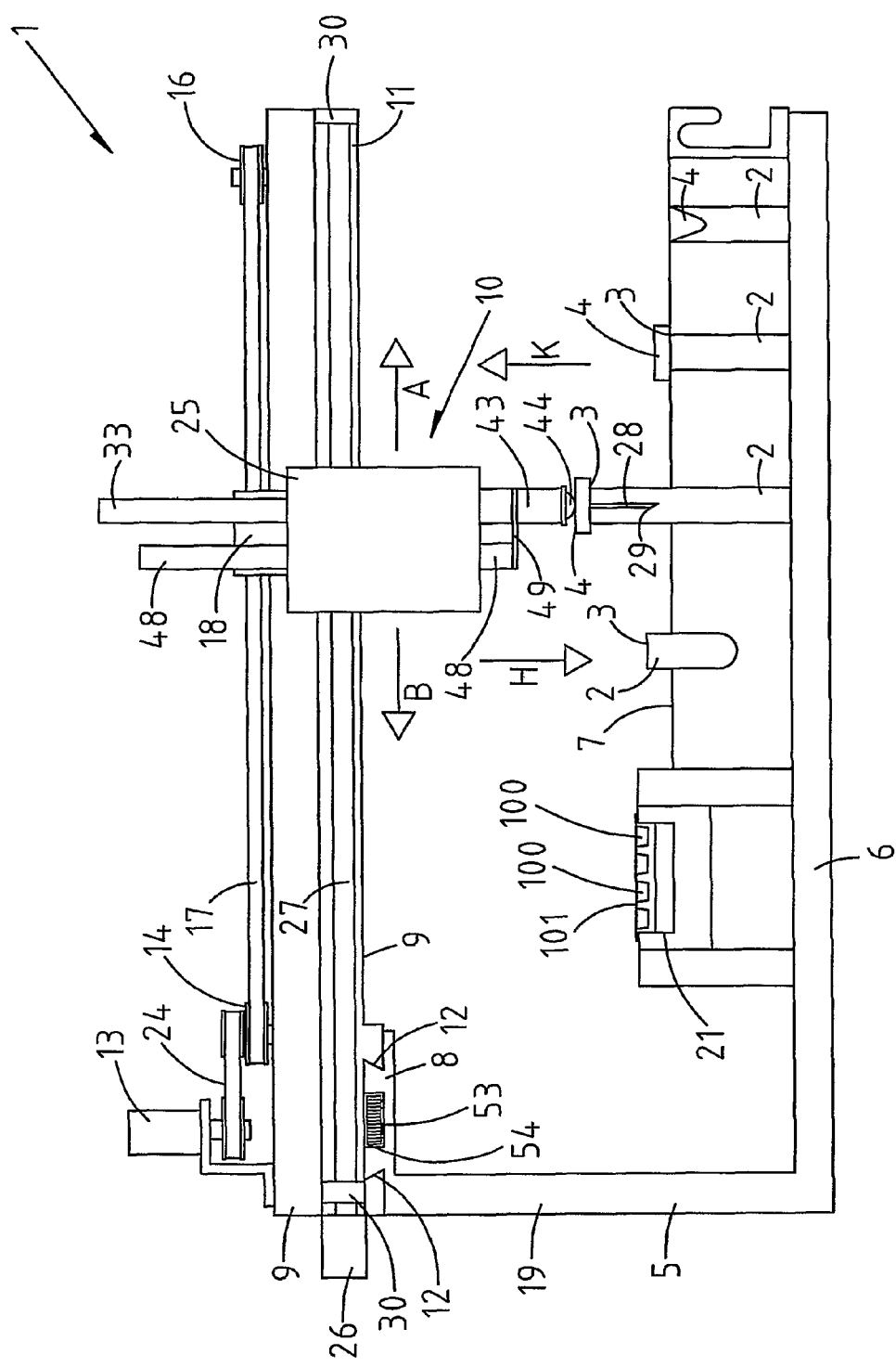
Figures 3, 6:
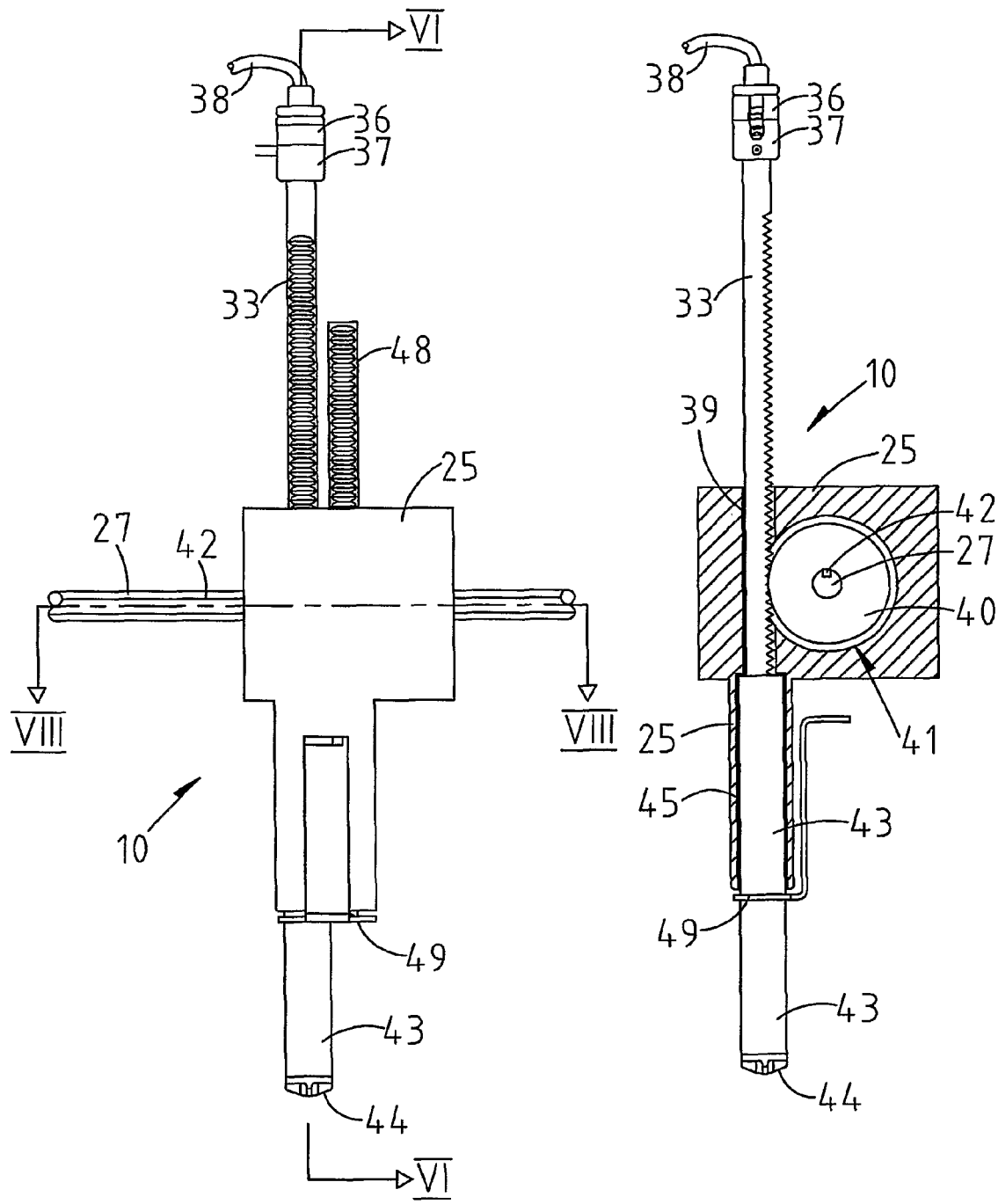
Figure 4:
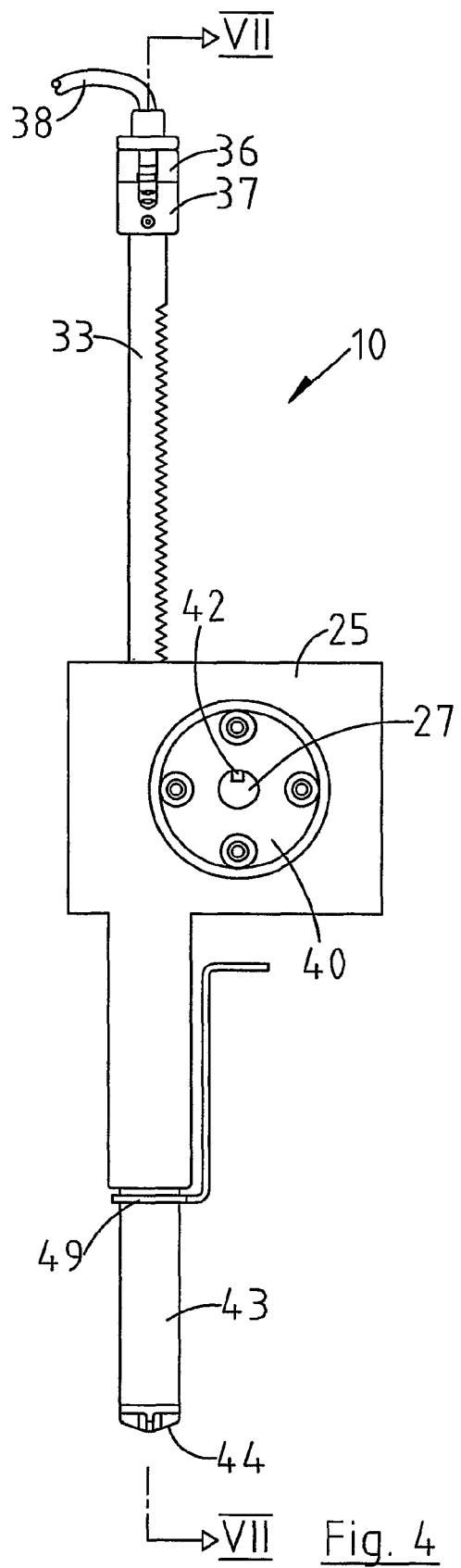
Figure 10:
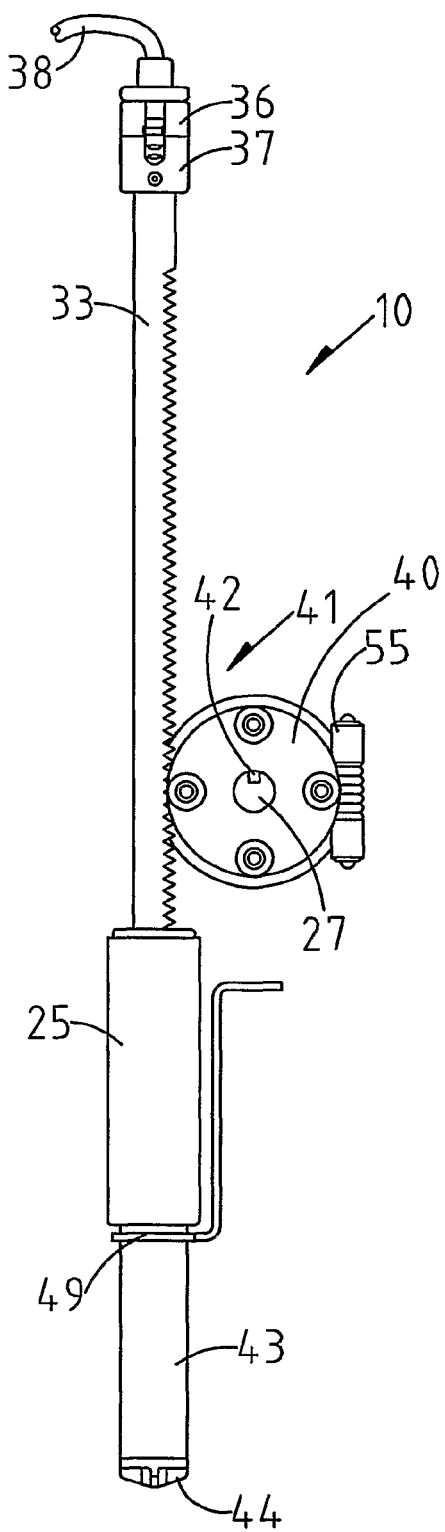
Figure 8:
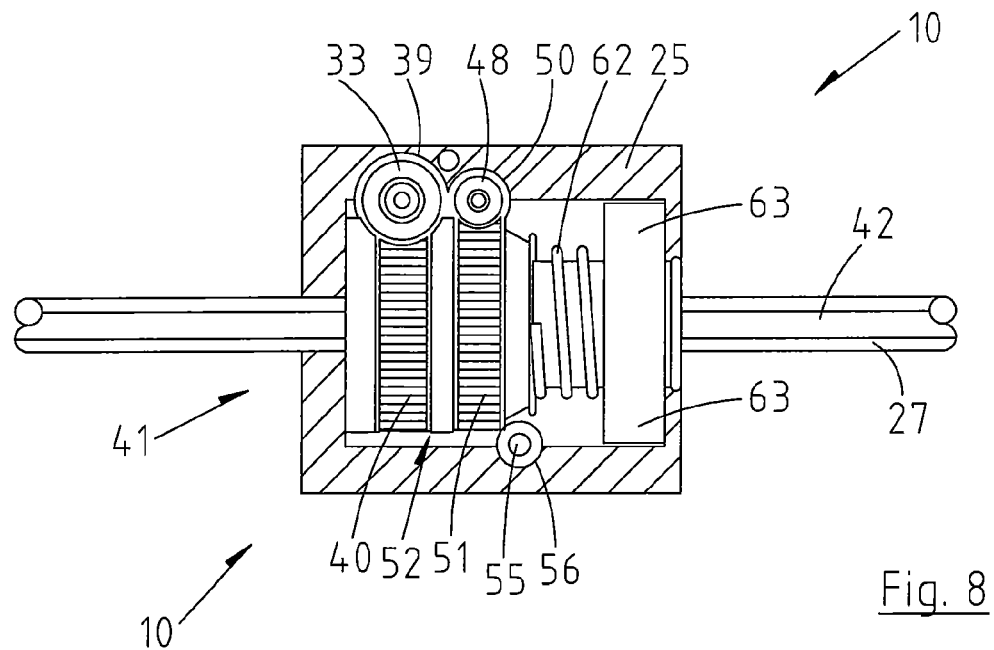
Figure 5:
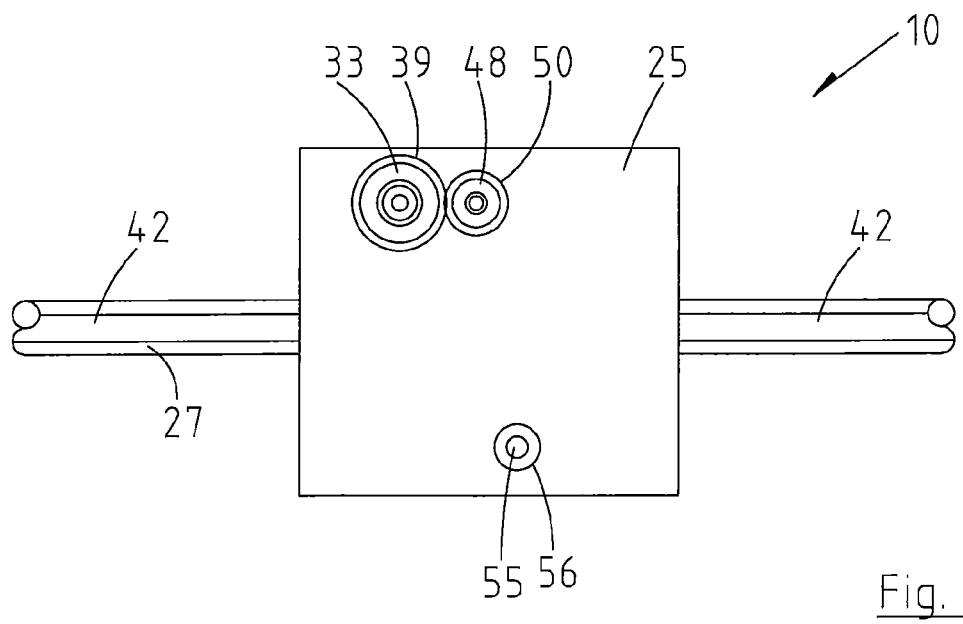
Figure 7:
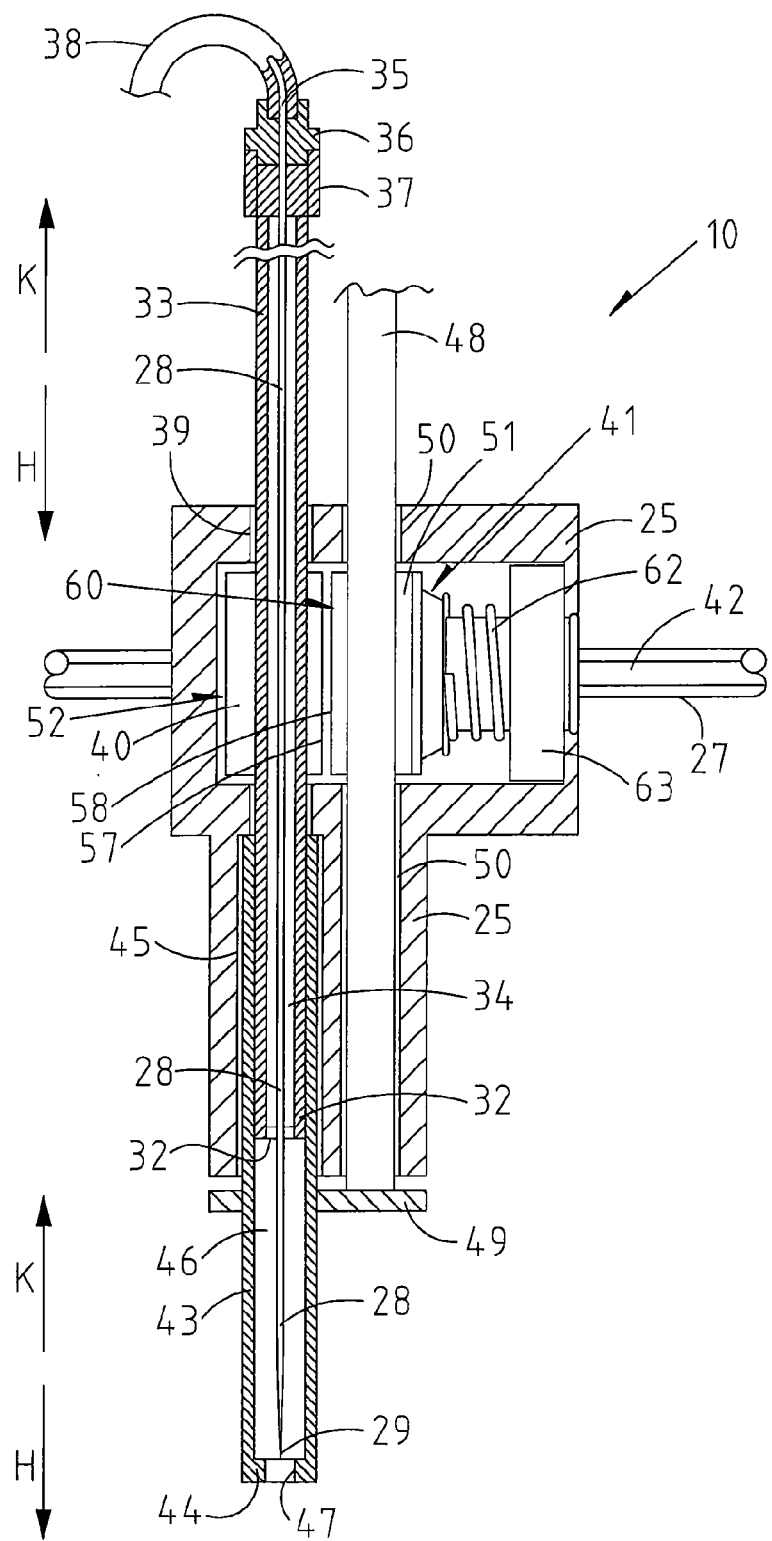
Figures 9, 11:
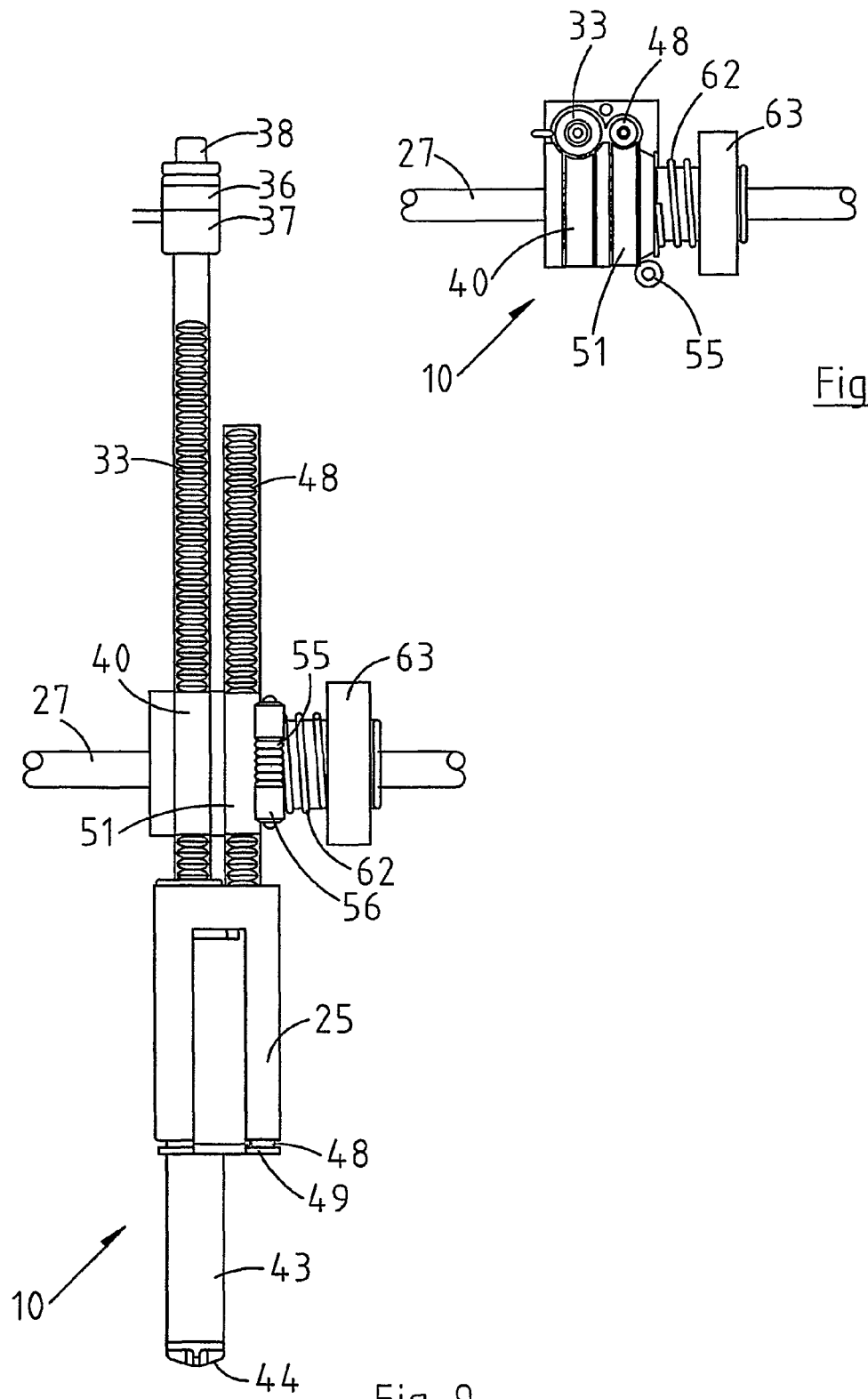
Figure 12:
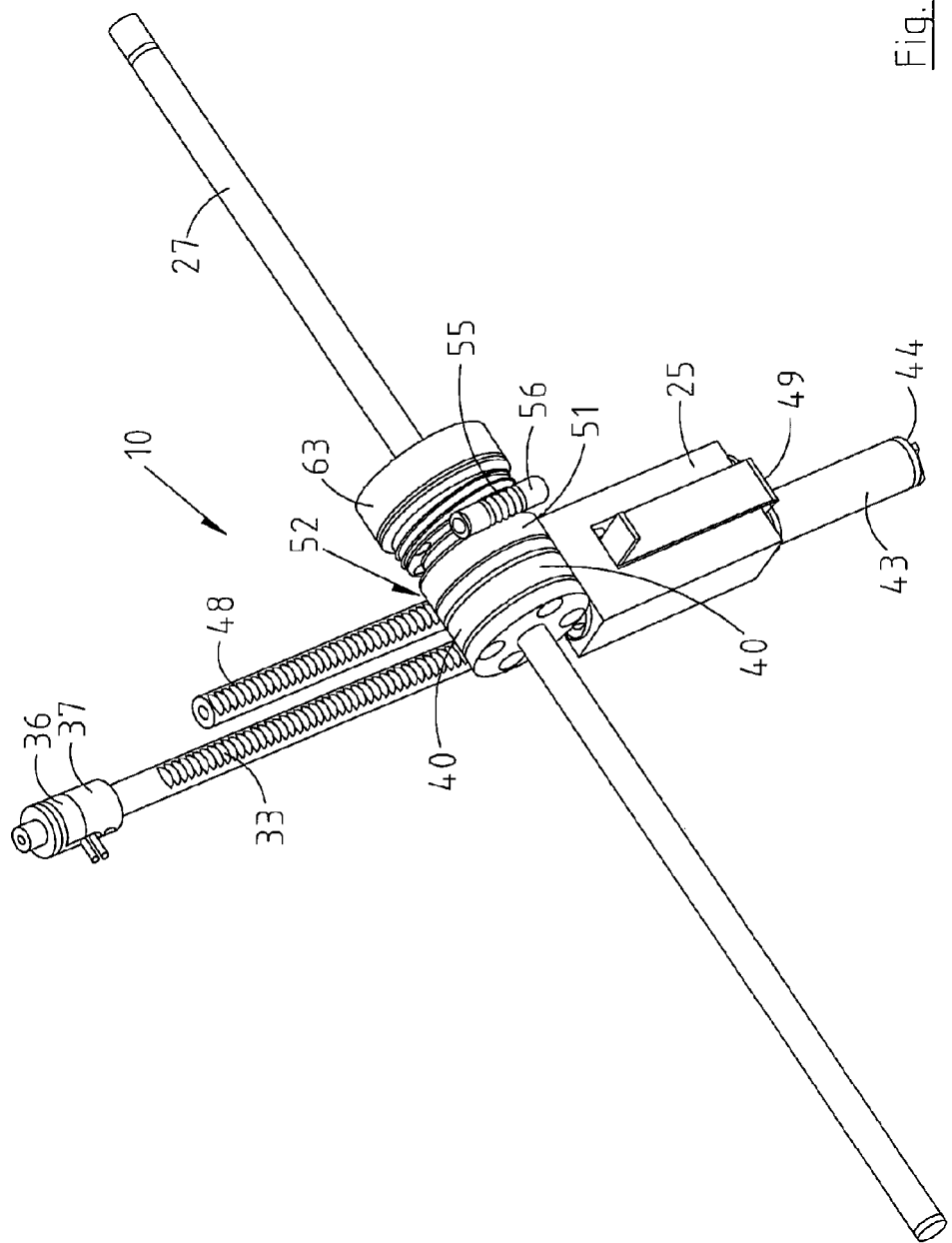
Figure 13:
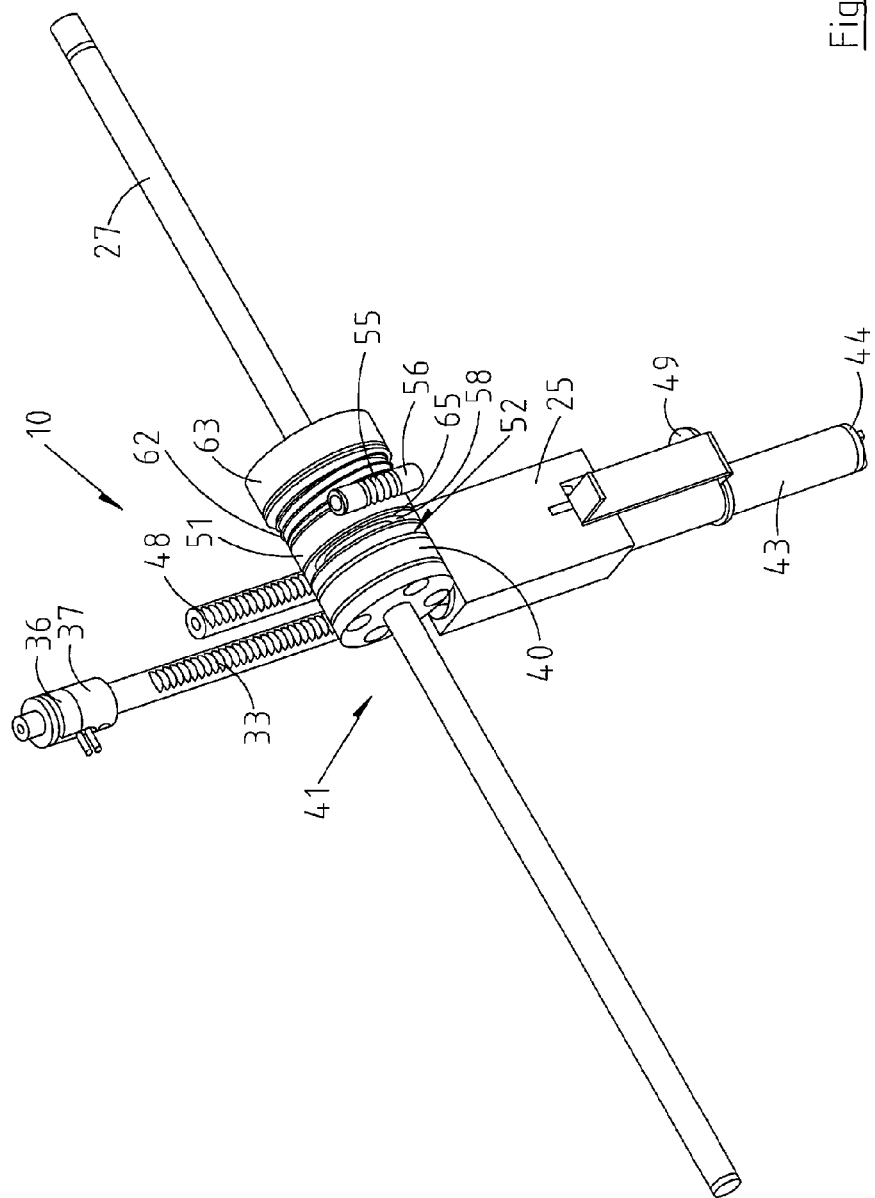
Figure 14:
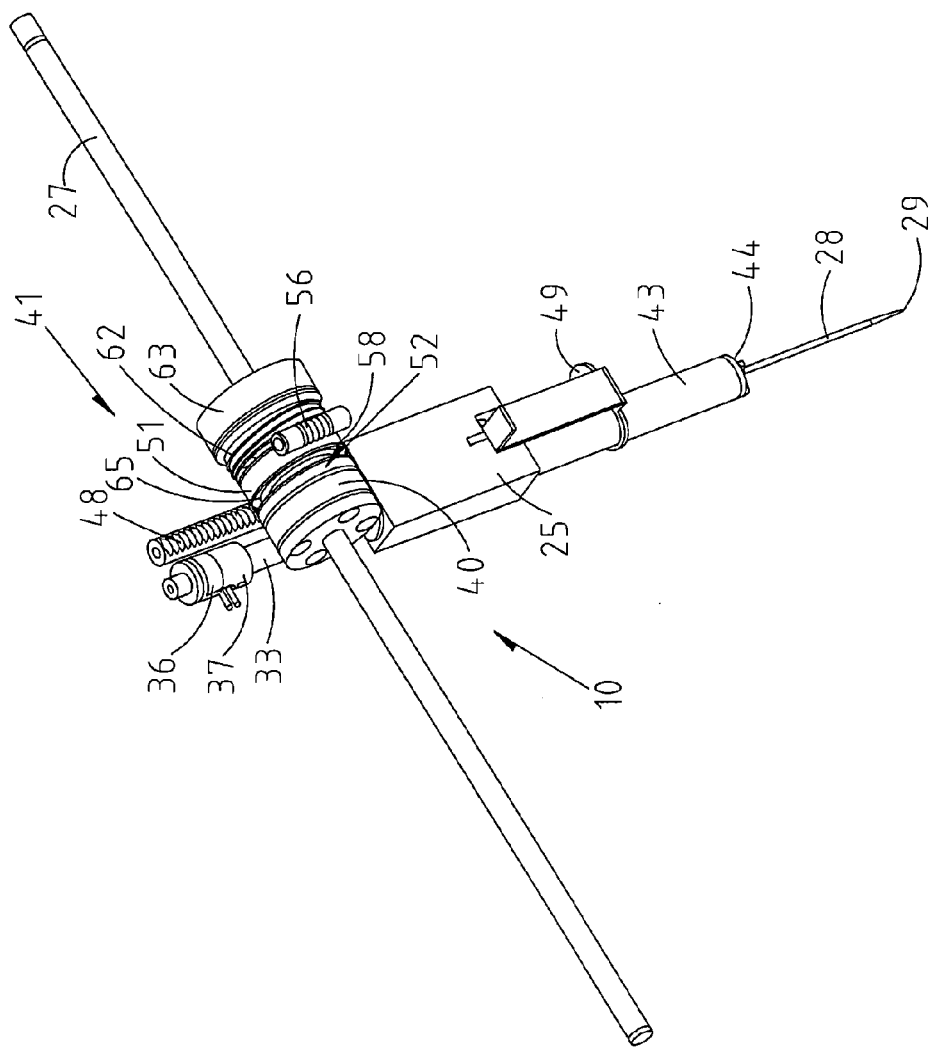
Figure 15:
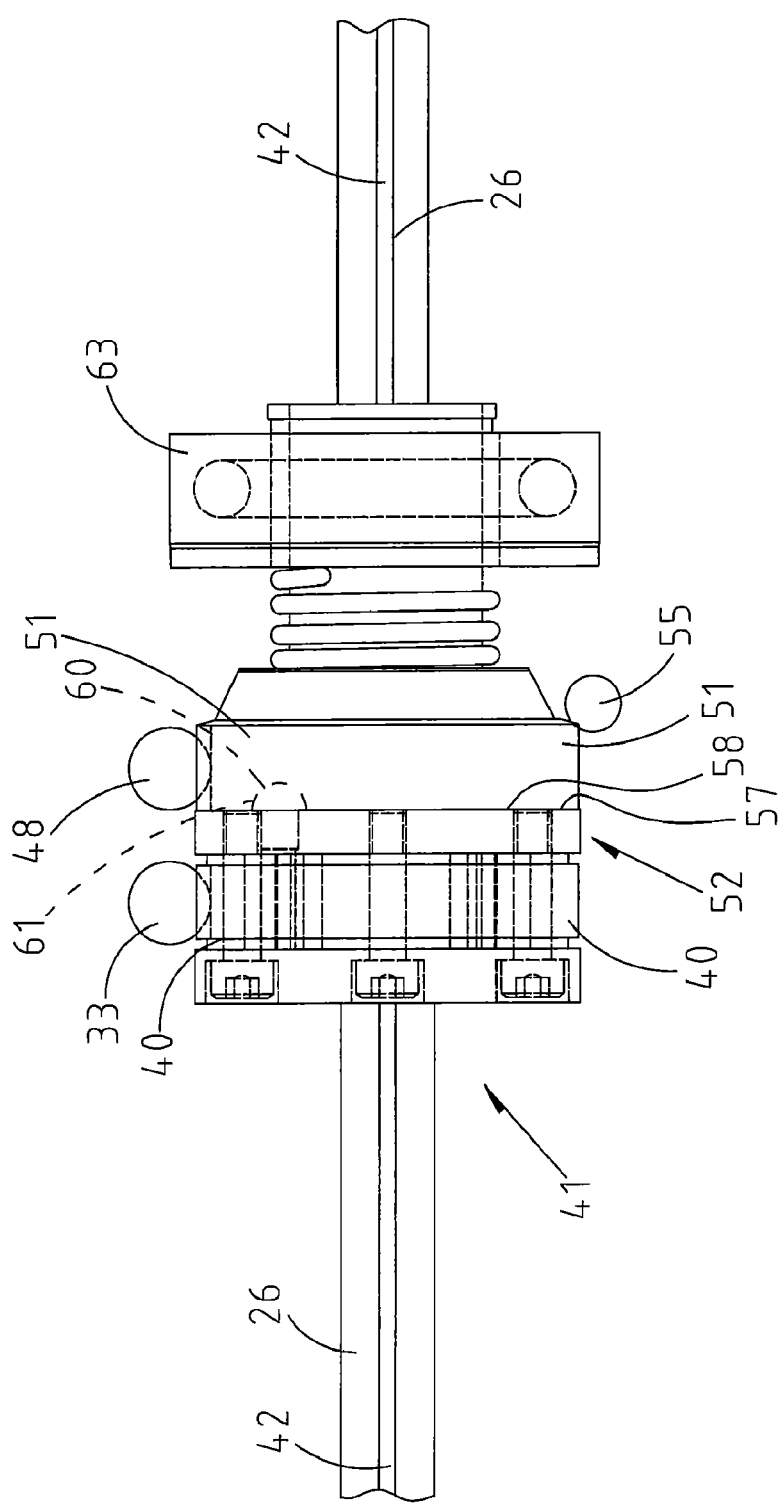
Figure 16:
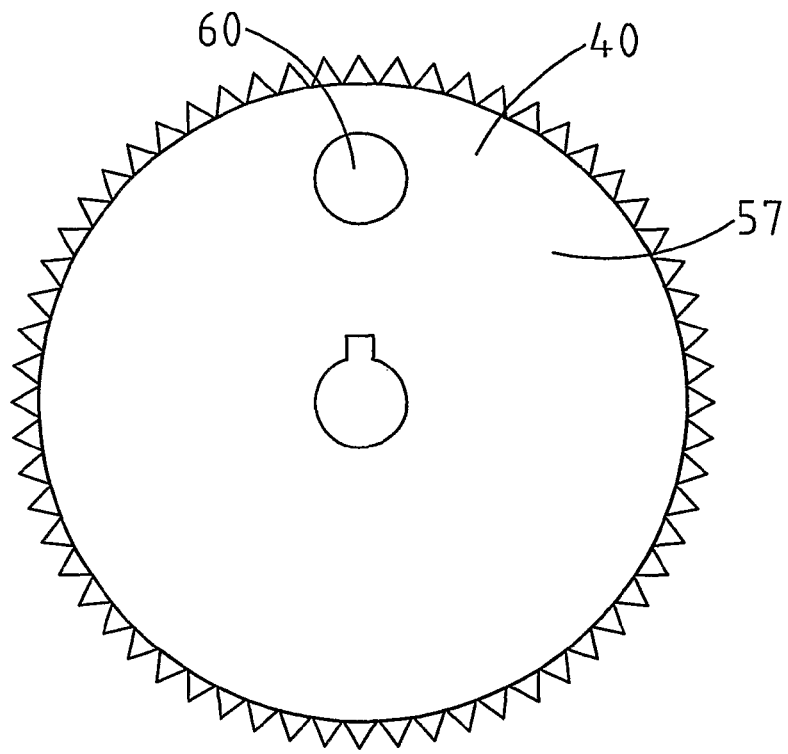
Figure 17:
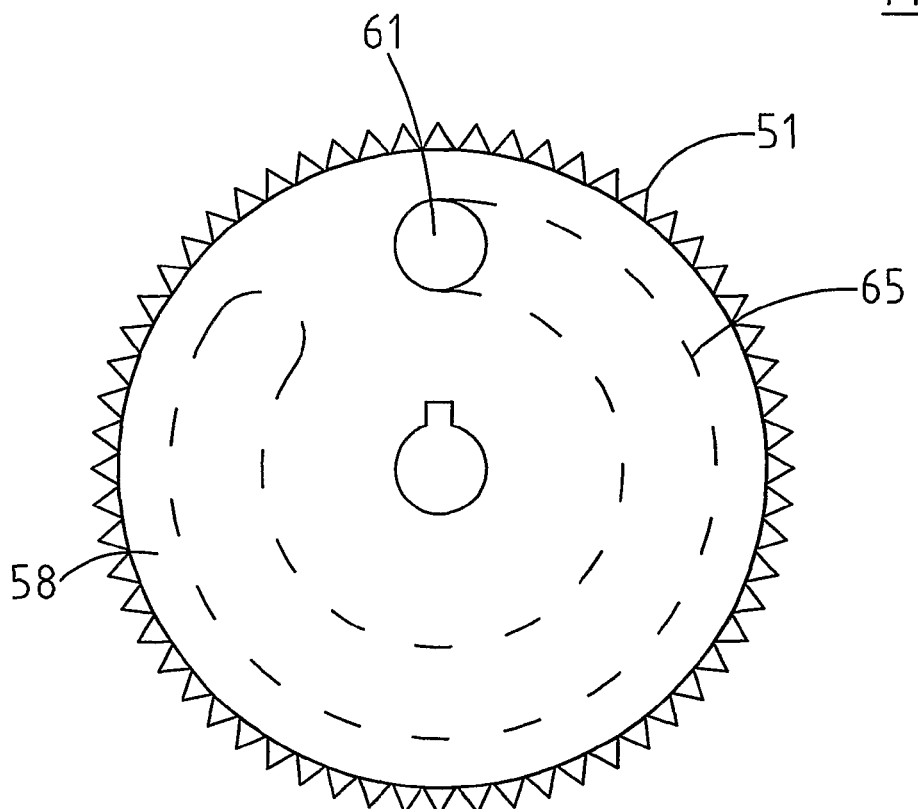

The invention will be more clearly understood from the following description of a preferred embodiment thereof, which is given by way of example only, with reference to the accompanying drawings, in which:

FIG. 1 is a general schematic top plan view of apparatus according to the invention which comprises a device also according to the invention for taking liquid samples from a plurality of containers supported in racks in the apparatus 1, FIG. 2 is a general schematic cross-sectional side elevational view of the apparatus of FIG. 1 on the line II-II of FIG. 1, FIG. 3 is a front elevational view of the device according to the invention for taking liquid samples in the apparatus of FIG. 1, FIG. 4 is a side elevational view of the device of FIG. 3, FIG. 5 is a top plan view of the device of FIG. 3, FIG. 6 is a transverse cross-sectional side elevational view of the device of FIG. 3 on the line VI-VI of FIG. 3, FIG. 7 is a transverse cross-sectional rear end elevational view of the device of FIG. 3 on the line VII-VII of FIG. 4, FIG. 8 is a transverse cross-sectional top plan view of the device of FIG. 3 on the line VIII-VIII of FIG. 3, FIG. 9 is a front elevational view of the device of FIG. 3 with a portion of a housing of the device of FIG. 3 removed, FIG. 10 is a side elevational view of the device of FIG. 3 with the portion of the housing also removed, FIG. 11 is a top plan view of the device of FIG. 3 with the portion of the housing also removed, FIG. 12 is a perspective view of the portion of the device of FIG. 3 illustrated in FIG. 9, FIG. 13 is a view similar to FIG. 12 illustrating portions of the device in a different position, FIG. 14 is a view similar to FIG. 12 illustrating portions of the device in a still further different position, FIG. 15 is an enlarged top plan view of a portion of the device of FIG. 3 with the housing removed therefrom, FIG. 16 is a side view of a detail of the device of FIG. 3, and FIG. 17 is a side view of another detail of the device of FIG. 3.

Referring to the drawings, there is illustrated apparatus according to the invention, indicated generally by the reference numeral 1, for facilitating withdrawing liquid samples from a plurality of containers, in this embodiment of the invention a plurality of vials 2 which are located in the apparatus 1, and for transferring the liquid samples to respective vessels, cuvettes, wells or the like, in this case wells 100 of well plates 101 for analysing the liquid samples therein. The well plates 101 are conveyed through the apparatus 1 as will be described below to suitable analytical apparatus, where the samples in the well plates 101 are analysed. Such analytical apparatus and well plates will be well known to those skilled in the art and further description thereof will not be provided. The vials 2 are of the type which typically are of glass terminating in an upper open mouth 3 which is closed by a closure element, typically provided by a closure cap 4 of a rubber or rubber type plastics material. The closure caps are penetrable by a pointed cannula, so that the pointed cannula can be urged through the closure cap 4 into the vial 2 for withdrawing a liquid sample therefrom. In general, such vials would contain small quantities of the liquid to be sampled, which typically, would be a bodily fluid, such as blood, blood plasma, urine and the like. The closure cap 4 typically forms a relatively tight friction type sealing fit around the cannula which tends to grip the cannula, thereby making it difficult to withdraw the cannula from the closure cap 4 without holding the closure cap 4 against the pull of the cannula as the cannula is being withdrawn therefrom. Indeed, while in this embodiment of the invention the apparatus 1 is described for facilitating the withdrawal of liquid samples from a plurality of vials 2, the apparatus according to the invention can likewise be used for discharging liquid samples into the vials 2.

The apparatus 1 comprises a housing 5 having a base 6 on which a plurality of transversely spaced apart parallel elongated longitudinally extending racks 7 are located for holding the vials 2 in an upright orientation spaced apart from each other. A guide way 21 supported on the base 6 extends transversely through the apparatus 1 along which the well plates 101 are guided through the apparatus 1 from an input end 22 to an output end 23. A conveying means comprising a suitable conveyor (not shown) conveys the guide plates 101 along the guide way 21 from the input end 22 to the output end 23, through which the well plates 101, the wells 100 of which contain samples to be analysed are transferred into the analytical apparatus.

A transverse member 8 supported on a side wall 19 which extends upwardly from the base 6 extends transversely of the racks 7 and supports a gantry 9 which extends parallel to the racks 7. A device also according to the invention and indicated generally by the reference numeral 10 for sequentially withdrawing the liquid samples from the respective vials 2 through the closure caps 4 of the respective vials 2 and for transferring the liquid samples into the wells 100 of the well plates 101 is mounted on the gantry 9. The device 10 is described in detail below.

The gantry 9 comprises a first guide means provided by an elongated carrier member 11 extending longitudinally relative to the racks 7 along which the device 10 is longitudinally slideable in the direction of the arrows A and B for guiding the device 10 into selective alignment with the vials 2 in the respective racks 7. A second guide means comprising a pair of spaced apart parallel transversely extending guide tracks 12 which are mounted on the transverse member 8 slideably engages the gantry 9 for guiding the gantry 9 in the direction of the arrows C and D transversely across the racks 7 for selective alignment of the device 10 with the respective racks 7.

A first drive means, namely, a first drive motor 13 located in the gantry 9 is provided for driving the device 10 along the carrier member 11 for selective alignment with the vials 2 in the respective racks 7. The drive motor 13 drives a toothed drive pulley 14, which in turn drives a toothed endless belt 15 extending around the drive pulley 14 and a toothed idler pulley 16 at the opposite end of the gantry 9 to that of the drive pulley 14. Drive is transmitted to the drive pulley 14 by the drive motor 13 through a belt drive 24. The device 10 is secured to one leg 17 of the belt 15 at 18 so that as the first drive motor 13 drives the leg 17 of the belt 15 in the direction of the arrows A and B, the device 10 is selectively alignable with the vials 2 in the rack 7. In this embodiment of the invention the first drive motor 13 is a stepper motor for facilitating incremental drive of the device 10 along the carrier member 11 in incremental steps for accurate alignment of the device 10 with the vials 2 in the racks 7 with which the device 10 is aligned.

A second drive means comprising a second drive motor 20 also located in the gantry 9 drives the gantry 9 transversely in the direction of the arrows C and D along the guide tracks 12 for selective alignment of the device 10 with the racks 7. The second drive motor 20 drives a pinion 53 which is engageable with a gear rack 54 extending along the transverse member 8 between the guide tracks 12 for driving the gantry 9 in the direction of the arrows C and D. In this embodiment of the invention the second drive motor is a stepper motor for facilitating incremental movement of the gantry 9 in the direction of the arrows C and D for accurately aligning the device 10 with the racks 7.

Referring now to FIGS. 3 to 17, the device 10 for withdrawing liquid samples from the vials 2 and transferring the liquid samples to the wells 100 of the well plate 101 will now be described. The device 10 comprises a housing 25 which is slideably engageable with the carrier member 11 and is slideable longitudinally along the carrier member 11 in the direction of the arrows A and B. A third drive means, namely, a third drive motor 26 located on the gantry 9 drives an elongated drive shaft 27 which extends along the carrier member 11, and which in turn drives a cannula 28 vertically upwardly and downwardly in the housing 25 for penetrating the closure caps 4 of the respective vials 2 and for urging the cannula 28 into the vials 2 for withdrawing the liquid samples therefrom. The cannula 28 and its mounting in the housing 25, which will be described in more detail below, terminates in a pointed tip 29 for puncturing the closure caps 4. The drive shaft 27 is rotatably carried in bearings 30 at respective opposite ends thereof which are mounted in the gantry 9. Bearings (not shown) located in the housing 25 accommodate rotation of the drive shaft 27 in the housing 25, and the bearings (not shown) in the housing 25 also accommodate sliding of the housing 25 and in turn the device 10 along the drive shaft 27.

The cannula 28 is housed within a vertically extending hollow tubular first gear rack 33 of circular transverse cross-section having an elongated bore 34 extending therethrough within which the cannula 28 is accommodated. The cannula 28 is secured to the first gear rack 33 at a top end 35 thereof by a gland nut 36 which engages a mounting member 37 mounted on the top end 35 of the first gear rack 33. The cannula 28 extends through the mounting member 37 and the gland nut 36 and is sealably secured to a tube 38 to which a vacuum is selectively applied for withdrawing liquid samples from the vials 2 into the cannula 28 for pipetting the liquid samples from the vials 2 to the wells 100 of the well plates 101. The cannula 28 extends downwardly through the bore 34 of the first gear rack 33 and exits the bore 34 at a bottom end 32 of the first gear rack 33.

The first gear rack 33 is slideable vertically in a first guide bore 39 extending through the housing 25. A drive transmission means, namely, a drive transmission 41 comprising a first drive element, namely, a first gearwheel 40 which is keyed to the drive shaft 27 transmits drive from the drive shaft 27 to the first gear rack 33 for urging the first gear rack 33 vertically downwardly and upwardly in the direction of the arrows H and K, respectively, through the first guide bore 39, for in turn urging the cannula 28 downwardly and upwardly in the direction of the arrows H and K for urging the cannula 28 into the vials 2 through the closure caps 4. A keyway 42 extending longitudinally along the drive shaft 27 slideably engages a key (not shown) which keys the first gearwheel 40 to the drive shaft 27.

An abutment means comprising a tubular abutment member 43 having an abutment end cap 44 engages the closure caps 4 of the vials 2 while the cannula 28 is being withdrawn through the closure caps 4 for preventing displacement of the closure caps 4 from the vials 2. The abutment member 43 is vertically slideable in a second guide bore 45 in the housing 25, which extends from and is coaxial with the first guide bore 39 in the housing 25. A bore 46 extending through the abutment member 43 slideably accommodates the first gear rack 33 within the abutment member 43 for facilitating relative movement between the first gear rack 33 and the abutment member 43, for in turn permitting relative movement between the cannula 28 and the abutment member 43, so that when the abutment member 43 is in engagement with one of the closure caps 4, the cannula 28 can move downwardly relative to the abutment member 43, for extending into the corresponding vial 2 through the closure cap 4. A cannula accommodating bore 47 in the abutment end cap 44 accommodates the cannula 28 through the abutment end cap 44 for facilitating relative movement of the cannula 28 relative to the abutment member 43.

A second gear rack 48 is coupled to the abutment member 43 through a coupling bracket 49, and the second gear rack 48 is vertically slideable upwardly and downwardly through a third guide bore 50 in the housing 25. The drive transmission 41 also comprises a second drive transmission element, namely, a second gearwheel 51 which is rotatably carried on the drive shaft 27 and is driven by the drive shaft 27 through the first gearwheel 40 and through a clutch means, namely, a dog clutch 52. The dog clutch 52, as will be described below, is adapted to decouple drive from the first gearwheel 40 to the second gearwheel 51 when the abutment member 43 engages the closure cap 4 of the vial 2 with which the device 10 is aligned, so that further driving of the first gearwheel 40 by the drive shaft 27 drives only the first gear rack 33 downwardly for in turn driving the cannula 28 into the vial 2 through the closure cap 4.

A retaining means, in this embodiment of the invention provided by a third gear rack 55 is fixedly mounted in a bore 56 in the housing 25, and is engageable by the second gearwheel 51 while the second gearwheel 51 is decoupled from the first gearwheel 40 by the clutch 52 for preventing rotation of the second gearwheel 51. Additionally, the second gearwheel 51 is simultaneously engageable with the third gear rack 55 and the second gear rack 48 so that while the second gearwheel 51 is decoupled from the first gearwheel 40 by the dog clutch 52, the second gear rack 48 is retained fixed with the abutment member 43 engaging the closure cap 4 of the corresponding vial 2. Thus, the abutment member 43 is retained in engagement with the closure cap 4 by the action of the third gear rack 55 on the second gearwheel 51 until the second gearwheel 51 is again recoupled with the first gearwheel 40 by the clutch 52. At that stage the cannula 28 has been withdrawn from the vial 2 and the closure cap 4 into the bore 46 of the abutment member 43, thereby permitting withdrawal of the cannula 28 from the vial 2 through the closure cap 4 without displacement of the closure cap 4.

Turning now to the dog clutch 52, and referring in particular to FIGS. 15 to 17, the dog clutch 52 is essentially formed by the first and second gearwheels 40 and 51 adjacent their respective abutting radial faces 57 and 58, respectively. An engagement means, in this embodiment of the invention a ball 60 which is housed in the first gearwheel 40 extends longitudinally outwardly of the radial face 57 of the first gearwheel 40 and is engageable with a corresponding substantially hemispherical recess 61 formed in the radial face 58 of the second gearwheel 51 for transferring drive from the first gearwheel 40 to the second gearwheel 51.

An urging means comprising a compression spring 62, see FIGS. 7 to 9 and 11, acting between the second gearwheel 51 and a thrust bearing 63 rotatable in the housing 25 and also rotatable on the drive shaft 27 urges the second gearwheel 51 into engagement with the first gearwheel 40 so that the radial faces 57 and 58 of the first and second gearwheels 40 and 41, respectively, abut each other with the ball 60 engaged in the recess 61 for transmitting drive from the first gearwheel 40 to the second gearwheel 51. A bearing means, namely, an arcuate bearing surface 65 extends circumferentially from the recess 61 around the radial face 58 of the second gearwheel 51 for slideably engaging the ball 60 while the second gearwheel 51 is decoupled from the first gearwheel 40.

The ratio of the linear movement of the first gear rack 33 for each incremental angular displacement of the first gearwheel 40 is such that the maximum distance of relative travel of the first gear rack 33 and in turn the cannula 28 relative to the abutment member 43 corresponds to less than a full 360° revolution of the first gearwheel 40. This thus avoids any danger of the ball 60 re-engaging the recess 61 during further downward movement of the first gear rack 33 and in turn the cannula 28 relative to the abutment member 43. Thus, on the abutment member 43 abutting the closure cap 4 of one of the vials 2, further rotation of the first gearwheel 40 causes the first gear rack 33 and in turn the cannula 28 to move downwardly relative to the abutment member 43 into the vial 2 while the abutment member 43 is engaging the closure cap 4. As the first gearwheel 40 continues to rotate after the abutment member 43 engages the closure cap 4, the ball 60 commences to disengage the recess 61, thereby urging the second gearwheel 51 axially towards the thrust bearing 63 against the action of the compression spring 62, and in turn into engagement with the third gear rack 55. In this position the second gearwheel 51 engages both the second and third gear racks 48 and 55, thereby retaining the abutment member 43 in engagement with the closure cap 4. Further rotation of the first gearwheel 40 causes the ball 60 to traverse the circumferential bearing surface 65 until the first gear rack 33 and the cannula 28 have traveled their maximum distance relative to the abutment member 43, and the cannula 28 is extended into the vial 2.

Reversing the drive on the drive shaft 27 reverses rotation of the first gearwheel 40, thereby urging the ball 60 in the reverse direction along the bearing surface 65 until the ball 60 re-engages the recess 61. At that stage the cannula has been withdrawn from the vial 2 and the closure cap 4 and is located within the bore 46 of the abutment member 43. Further reverse rotation of the drive shaft 27 urges the cannula 28 and the abutment member 43 simultaneously upwardly away from the closure cap 4 and the vial 2.

Accordingly, the drive transmission 41 which transmits drive from the third drive motor 26 through the drive shaft 27 to the cannula 28 and the abutment member 43 is responsive to the abutment member 43 engaging the closure cap 4 of the vial 2 with which the device 10 is aligned for urging the cannula 28 relative to the abutment member 43 into the vial 2, and furthermore, the drive transmission 41 is responsive to the cannula 28 being withdrawn from the vial 2 and the closure cap 4 for permitting simultaneous movement of the cannula 28 and the abutment member 43 away from the vial 2.

The first and second gear racks 33 and 48 are set relative to the first and second gearwheels 40 and 51 so that when the ball 60 is engaged in the recess 61 with the dog clutch 52 coupling the first and second gearwheels 40 and 51, the first gear rack 33 is located relative to the second gear rack 48 so that the cannula 28 is located fully within the bore 46 of the abutment member 43 as illustrated in FIG. 7. Thus, while the first and second gearwheels 40 and 51 are coupled by the dog clutch 52, the cannula 28 and the abutment member 43 move simultaneously with each other with the cannula 28 located fully within the bore 46 of the abutment member 43.

In use, with vials 2 loaded into the racks 7 of the apparatus 1 and the tube 38 coupled to a suitably controlled vacuum system, the apparatus 1 is ready for use. With the cannula 28 located within the abutment member 43, and the abutment member 43 raised above the level of the vials 2, in order to withdraw a liquid sample from a selected one of the vials 2, the second drive motor 20 is operated for urging the gantry 9 along the guide tracks 12 to align the device 10 with the rack 7 within which the selected vial 2 is located. The first drive motor 13 is then operated for urging the device 10 along the carrier member 11 to align the device 10 with the selected vial 2 in the selected rack 7. It will be appreciated that the first and second drive motors 13 and 20 could be simultaneously operated for aligning the device 10 with the selected vial 2.

With the device 10 aligned with the selected vial 2, the third drive motor 26 is operated for driving the drive shaft 27 for in turn driving the first gearwheel 40 and in turn the second gearwheel 51 for simultaneously driving the first and second gear racks 33 and 48 downwardly for in turn simultaneously driving the cannula 28 and the abutment member 43 downwardly until the abutment member 43 engages the closure cap 4 of the selected vial 2. The resistance encountered by the abutment member 43 on engaging the closure cap 4 of the selected vial 2 causes the dog clutch 52 to decouple the second gearwheel 51 from the first gearwheel 40. As the ball 60 disengages the recess 61 and engages the bearing surface 65, the second gearwheel 51 is urged into engagement with the third gear rack 55, while still in engagement with the second gear rack 48. This, thus, prevents further downward movement of the abutment member 43 and retains the abutment member 43 in engagement with the closure cap 4.

Further rotation of the drive shaft 27 drives the first gearwheel 40 and in turn drives the first gear rack 33 downwardly, thereby urging the cannula 28 through the cannula accommodating bore 47 in the abutment end cap 44 of the abutment member 43 and into engagement with the closure cap 4. The pointed tip 29 of the cannula 28 pierces the closure cap 4. Further downward movement of the first gear rack 33 urges the cannula 28 through the closure cap 4 and into the selected vial 2. When the cannula 28 has been urged a sufficient distance downwardly into the vial 2 for withdrawing the liquid sample, the vacuum is applied to the tube 38 for withdrawing the liquid sample of a desired volume into the cannula 28.

With the liquid sample of the desired volume in the cannula 28, the vacuum is isolated from the tube 38. The drive shaft 27 is operated in reverse for urging the first gear rack 33, and in turn the cannula 28 upwardly until the cannula 28 has disengaged the closure cap 4 and is located within the bore 46 of the abutment member 43. At this stage the dog clutch 52 recouples the second gearwheel 51 to the first gearwheel 40, and the second gearwheel 51 disengages the third gear rack 55. Further reverse rotation of the drive shaft 27 simultaneously rotates the first and second gearwheels 40 and 51, and in turn urges the first and second gear racks 33 and 48 simultaneously upwardly for in turn urging the cannula 28 and the abutment member 43 simultaneously upwardly away from the closure cap 4 and the vial 2. The first and second drive motors 13 and 20 are simultaneously or sequentially operated for aligning the device 10 with a selected one of the wells 100 of the well plates 101 to which the liquid sample is to be transferred. On the device 10 being aligned with the selected well 100, the drive motor 26 is operated for driving the cannula 28 and the abutment member 43 downwardly towards the selected well 100, and the liquid sample is discharged from the cannula 28 into the well 100.

At this stage the apparatus 1 is ready to withdraw a liquid sample from the next to be selected of the vials 2, and operation of the apparatus 1 for withdrawing the next liquid sample is similar to that already described.

The advantages of the invention are many. A particularly important advantage of the invention is that the device 10, and the apparatus 1 can be used for taking samples from vials of different height, where the closure caps 4 thereof are at different distances from the device 10. This is achieved by virtue of the fact that the first and second gear racks 33 and 48 are simultaneously urged downwardly by the first and second gearwheels 40 and 51 until the abutment member 43 engages the closure cap 4 of the vial 2 with which the device 10 is aligned. Only at that stage when the abutment member 43 is in engagement with the closure cap 4 is the cannula 28 urged outwardly of the abutment member 43 to penetrate the closure cap 4 into the vial 2. Thus, irrespective of the distance from which the closure cap 4 is located relative to the device 10, provided the closure cap 4 is within the vertical downward travel of the abutment member 43, the cannula 28 remains within the abutment member 43 until the closure cap 4 is engaged by the abutment member 43, and only then is the cannula 28 urged outwardly through the closure cap 4 into the vial 2.

A further and also particularly important advantage of the invention is the fact that the retaining means, which in this embodiment of the invention is described as being the third gear rack 55, is provided for retaining the abutment member 43 in engagement with the closure cap until the cannula 28 has been withdrawn from the closure cap. Again, since relative movement of the cannula 28 does not occur until the abutment member 43 engages the closure cap 4, the second gearwheel 51 will always be engaged with the third gear rack 55 during relative movement of the cannula 28 relative to the abutment member 43, and thus the abutment member 43 will be retained in engagement with the closure cap 4 until the cannula 28 has been withdrawn into the abutment member 43.

While the apparatus according to the invention and the device according to the invention have been described for use in withdrawing liquid samples from vials, it will be readily apparent to those skilled in the art that the apparatus may be used for withdrawing liquid samples from any type of container, and indeed, it will be appreciated by those skilled in the art that the apparatus and device may be scaled up or scaled down, depending on the general sizes of the containers with which the apparatus and device is to be used. It will also be appreciated that the apparatus and the device according to the invention may be used for discharging by way of pipetting a liquid sample into a vial or other such container, or from one vial to another.

While the apparatus and the device according to the invention have been described for use in withdrawing a liquid sample from a vial having an open mouth which is closed by a penetrable closure element, it is envisaged that the apparatus and the device according to the invention may be used for withdrawing liquid samples from containers which may not have a closure element closing an open mouth of the container. In which case, the abutment member would act as a probe to engage the container adjacent the open mouth, and once the container had been engaged by the abutment member adjacent the open mouth, the cannula could then be extended from the abutment member into the container for withdrawing the liquid sample. This would thus prevent the cannula being urged outwardly of the abutment member until the container had been engaged by the abutment member.

It will also be appreciated that in certain cases, the abutment means instead of abutting the closure cap of the selected vial, may instead abut or engage the vial, and if the abutment means abuts or engages the vial, it is envisaged that the abutment means would, although not necessarily, engage the vial adjacent the open mouth.

The invention claimed is:
1. Apparatus for withdrawing liquid samples from respective ones of a plurality of containers or for discharging liquid samples into respective ones of a plurality of containers, the apparatus comprising:

a rack for holding the containers,
a device for withdrawing a liquid sample from a selected one of the containers or for discharging a liquid sample into a selected one of the containers, the device being mounted on the apparatus above the rack, and being moveable relative to the rack for selective alignment with a selected one of the containers, the device comprising:
a cannula adapted for extending into the selected container and to withdraw or discharge the liquid sample from or to the selected container,
an abutment means adapted to engage one of the selected container and a closure element thereof,
a drive shaft,
a first drive transmission element mounted on the drive shaft for receiving drive therefrom for urging the cannula into the selected container,
a second drive transmission element for urging the abutment means into engagement with one of the selected container and the closure element thereof, and
a clutch means coupling the second drive transmission element to the first drive transmission element for transmitting drive from the drive shaft to the abutment means through the first and second drive transmission element to simultaneously urge the cannula and the abutment means towards the selected container, the clutch means being responsive to the abutment means engaging one of the selected container and the closure element thereof for decoupling the second drive transmission element from the first drive transmission element, so that the cannula is urgeable relative to the abutment means by the first drive means into the selected container,
wherein the clutch means is formed by the first and second drive transmission elements and comprises an engagement means extending from one of the first and second drive transmission elements for releasably engaging a corresponding receiving means on the other one of the first and second drive transmission elements for selectively transmitting drive from the first drive transmission element to the second drive transmission element.

2. Apparatus as claimed in claim 1 in which the rack is an elongated rack, and a first guide means is provided for guiding the device along the rack for sequential selective alignment of the device with the respective containers in the rack, a first drive means being provided for driving the device along the first guide means.

3. Apparatus as claimed in claim 2 in which a plurality of spaced apart parallel elongated racks are located in the apparatus, and a second guide means is provided for guiding the device transversely across the racks for selective alignment therewith.

4. Apparatus as claimed in claim 3 further comprising a base and the racks for the containers are mounted on the base, and a gantry is supported over the racks, the first guide means extending longitudinally along the gantry, the device being mounted on the gantry and being urgeable along the gantry on the first guide means.

5. Apparatus as claimed in claim 4 in which a second drive means is provided, and the gantry is urgeable along the second guide means by the second drive means for selective alignment of the device with the respective racks.

6. Apparatus as claimed in claim 1 in which a retaining means is provided for retaining the abutment means in engagement with one of the selected container and the closure element thereof during movement of the cannula relative to the abutment means in a direction outwardly of the container until the cannula has disengaged the closure element.

7. Apparatus as claimed in claim 6 in which the retaining means is co-operable with the second drive transmission element while the second drive transmission element is decoupled from the first drive transmission element by the clutch means for retaining the abutment means in engagement with one of the selected container and the closure element thereof.

8. Apparatus as claimed in claim 6 in which the second drive transmission element comprises a second gearwheel engageable with a second gear rack secured to the abutment means.

9. Apparatus as claimed in claim 8 in which the retaining means comprises a third gear rack with which the second gearwheel is engageable, the third gear rack being fixed relative to the second gearwheel for preventing rotation thereof when the second gearwheel is in engagement therewith.

10. Apparatus as claimed in claim 9 in which the second gearwheel is simultaneously engageable with the second gear rack and the third gear rack while the second drive transmission element is decoupled from the first drive transmission element by the clutch means.

11. Apparatus as claimed in claim 6 in which the first drive transmission element comprises a first gearwheel engageable with a first gear rack secured to the cannula.

12. Apparatus as claimed in claim 11 in which the first gearwheel is configured so that the ratio of the linear distance travelled by the first gear rack for each unit angular displacement of the first gearwheel is such that the angular displacement of the first gearwheel required to drive the first gear rack a distance corresponding to the maximum distance of relative movement between the cannula and the abutment means in a direction inwardly into the container is less than 360°.

13. Apparatus as claimed in claim 1 in which the first drive transmission element is keyed to the drive shaft, and the second drive transmission element is rotatably mounted on the drive shaft.

14. Apparatus as claimed in claim 1 in which the cannula is adapted for penetrating the closure elements of the containers to extend into the selected one of the containers through the closure element thereof.

15. Apparatus as claimed in claim 14 in which the clutch means is responsive to the abutment means abutting the closure element of the selected container for decoupling the second drive transmission element from the first drive transmission element, so that the cannula is urgeable by the first drive transmission element relative to the abutment means through the closure element into and out of the selected container with the abutment means in engagement with the closure element for preventing displacement of the closure element.

16. Apparatus as claimed in claim 1 in which the cannula is adapted for withdrawing liquid samples from the respective containers.

17. Apparatus as claimed in claim 1 in which the clutch means is responsive to the distance through which the cannula is moved relative to the abutment means in a direction outwardly out of the selected container being substantially similar to the distance through which the cannula has been previously moved relative to the abutment means in a direction inwardly into the selected container after engagement of the abutment means with one of the selected container and the closure element thereof for recoupling the second drive transmission element to the first drive transmission element.

18. Apparatus as claimed in claim 1 in which a bearing means extends from the receiving means on the one of the first and second drive transmission elements for accommodating relative movement between the engagement means and the bearing means.

19. Apparatus as claimed in claim 18 in which the bearing means comprises a bearing surface of length extending from the receiving means a distance sufficient to accommodate the maximum distance of relative movement of the cannula relative to the abutment means in a direction inwardly into the container.

20. Apparatus as claimed in claim 1 in which the engagement means and the receiving means are located on respective adjacent radial faces of the first and second drive transmission elements.

21. Apparatus as claimed in claim 1 in which a third drive means is provided for driving the drive shaft.

22. Apparatus as claimed in claim 1 in which an urging means is provided for urging the engagement means into engagement with the receiving means.

* * * * *